United States Patent
Ortiz et al.

(10) Patent No.: US 10,820,936 B2
(45) Date of Patent: Nov. 3, 2020

(54) PEDICLE SCREW REMOVAL TOOL AND METHOD OF USE

(71) Applicant: ORTHOPEDIC RENOVATION TECHNOLOGIES, LLC, Helotes, TX (US)

(72) Inventors: Rene Ortiz, Helotes, TX (US); Alejandro Rene Ortiz, Helotes, TX (US)

(73) Assignee: ORTHOPEDIC RENOVATION TECHNOLOGIES, LLC, Helotes, TX (US)

(*) Notice: Subject to any disclaimer, the term of this patent is extended or adjusted under 35 U.S.C. 154(b) by 407 days.

(21) Appl. No.: 15/344,152

(22) Filed: Nov. 4, 2016

(65) Prior Publication Data

US 2018/0125559 A1    May 10, 2018

(51) Int. Cl.
　　*A61B 17/88*　　(2006.01)
　　*A61B 17/86*　　(2006.01)
　　*A61B 17/70*　　(2006.01)

(52) U.S. Cl.
　　CPC ...... *A61B 17/8875* (2013.01); *A61B 17/7032* (2013.01); *A61B 17/7076* (2013.01);
　　(Continued)

(58) Field of Classification Search
　　CPC ............ A61B 17/8875; A61B 17/8615; A61B 17/861; A61B 17/7079; A61B 17/7076;
　　(Continued)

(56) References Cited

U.S. PATENT DOCUMENTS

| 1,741,810 | A | * | 12/1929 | Bidal | B25G 1/005 |
| | | | | | 81/177.2 |
| 1,775,402 | A | * | 9/1930 | Mandl | B25B 13/56 |
| | | | | | 81/177.75 |

(Continued)

FOREIGN PATENT DOCUMENTS

| CN | 203226891 | 10/2013 |
| CN | 204446088 | 7/2015 |

(Continued)

OTHER PUBLICATIONS

CN 203226891 machine translation, Aug. 24, 2017.
CN 204446088 machine translation, Aug. 24, 2017.

*Primary Examiner* — Jessica Weiss
(74) *Attorney, Agent, or Firm* — Schultz & Associates, P.C.

(57) ABSTRACT

Disclosed is a universal pedicle screw removal tool comprising a tapered shaft having an "L" shaped tip on one end and a generally square head on an opposite end. A lower section leads to a tapered section which is connected to a handle. The handle may include a set of serrations to provide increased grip. The handle is connected to the head. The tip is sized to engage the channel of a tuliped pedicle screw while the head is sized to engage a ratchet or other torque producing tool. In an alternate embodiment, the tip is "T" shaped. In another alternate embodiment, the handle section includes opposing members extending from the shaft to form a "T" shaped handle. In use, the tip is inserted into the channel of a tuliped pedicle screw while the shaft is rotated to unscrew the pedicle screw from a patient's bone.

12 Claims, 7 Drawing Sheets

(52) U.S. Cl.
CPC ........ *A61B 17/7082* (2013.01); *A61B 17/861* (2013.01); *A61B 17/8615* (2013.01); *A61B 17/8877* (2013.01)

(58) Field of Classification Search
CPC .............. A61B 17/8877; B25B 13/481; B25B 23/0021; B25B 23/0035; B25G 1/04; B25G 1/005; A61C 8/009; A61C 8/0092; A61C 8/0089; A61C 8/0096
USPC ............ 606/70–71, 280–299, 201, 217, 226, 606/235–243, 104; 81/177.2; 132/73.5–76.5; 433/124
See application file for complete search history.

(56) References Cited

U.S. PATENT DOCUMENTS

| | | | | |
|---|---|---|---|---|
| 1,835,315 | A * | 12/1931 | McLay | B25G 1/007 81/177.9 |
| 2,530,914 | A * | 11/1950 | Simmons | B25B 13/5091 81/52 |
| 2,697,370 | A * | 12/1954 | Brooks | B25B 13/466 81/58 |
| 2,814,322 | A * | 11/1957 | Kupfrian | B25B 13/481 81/64 |
| 3,882,753 | A * | 5/1975 | Svensen | B25B 13/06 81/177.7 |
| 3,972,252 | A * | 8/1976 | Hunter | B25B 13/467 81/57.29 |
| 4,334,445 | A * | 6/1982 | Timewell | B25G 1/063 81/177.7 |
| 5,148,724 | A * | 9/1992 | Rexford | B25B 13/06 81/124.4 |
| D334,516 | S * | 4/1993 | Tsunoda | D8/29 |
| 5,536,268 | A | 7/1996 | Griss | |
| 5,899,901 | A * | 5/1999 | Middleton | A61B 17/7032 606/102 |
| 5,950,507 | A * | 9/1999 | Wolfe | B25B 21/007 81/177.2 |
| 6,089,128 | A * | 7/2000 | Kopyless | B25B 13/48 81/124.7 |
| 6,286,396 | B1 * | 9/2001 | Johnson | B25B 9/00 81/177.2 |
| 6,427,564 | B1 * | 8/2002 | Nelson | B25G 1/005 81/177.1 |
| 7,470,279 | B2 | 12/2008 | Jackson | |
| 7,677,140 | B2 * | 3/2010 | Hull | B25B 13/461 16/429 |
| 8,065,938 | B1 * | 11/2011 | Kravitch | B25B 13/48 81/177.2 |
| 8,117,951 | B2 * | 2/2012 | Brobst | B25G 3/38 81/177.2 |
| 8,202,303 | B2 | 6/2012 | Zehnder | |
| D680,396 | S * | 4/2013 | He | D8/21 |
| 8,414,628 | B2 | 4/2013 | Melkent | |
| 8,469,960 | B2 | 6/2013 | Hutton et al. | |
| 8,617,210 | B2 | 12/2013 | Sicvol et al. | |
| 8,709,015 | B2 * | 4/2014 | Kolb | A61B 17/7032 606/246 |
| 8,845,649 | B2 | 9/2014 | Jackson | |
| 8,852,239 | B2 | 10/2014 | Jackson et al. | |
| 8,986,349 | B1 | 3/2015 | German et al. | |
| 9,033,988 | B2 * | 5/2015 | Gephart | A61B 17/3421 606/86 A |
| 9,101,416 | B2 | 8/2015 | Dunbar, Jr. et al. | |
| 9,125,694 | B2 | 9/2015 | Butler et al. | |
| 9,198,698 | B1 | 12/2015 | Doose et al. | |
| 9,241,738 | B2 | 1/2016 | Quevedo et al. | |
| 9,289,249 | B2 | 3/2016 | Ramsey | |
| 9,295,500 | B2 | 3/2016 | Marigowda | |
| 9,295,501 | B2 | 3/2016 | Hammer | |
| 9,320,550 | B2 | 4/2016 | Hutton et al. | |
| 9,326,798 | B2 | 5/2016 | Kolb et al. | |
| 2003/0216743 | A1 * | 11/2003 | Hoffman | A61B 17/0401 606/99 |
| 2003/0217623 | A1 * | 11/2003 | Brown | B25B 13/48 81/437 |
| 2005/0140062 | A1 * | 6/2005 | Shimomura | B22C 7/06 264/334 |
| 2005/0149052 | A1 | 7/2005 | Meek | |
| 2005/0273167 | A1 * | 12/2005 | Triplett | A61B 17/1671 623/17.11 |
| 2008/0154280 | A1 * | 6/2008 | Schumacher | A61B 17/7083 606/104 |
| 2009/0187194 | A1 * | 7/2009 | Hamada | A61B 17/7001 606/104 |
| 2009/0217789 | A1 * | 9/2009 | Chang | B25B 13/465 81/60 |
| 2009/0248088 | A1 | 10/2009 | Biedermann | |
| 2013/0090698 | A1 * | 4/2013 | Nuckley | A61B 17/7082 606/308 |
| 2013/0331892 | A1 | 12/2013 | Peterson et al. | |
| 2014/0026724 | A1 * | 1/2014 | Broadaway | B25G 1/00 81/489 |
| 2014/0288567 | A1 * | 9/2014 | Kroll | A61B 17/8886 606/104 |
| 2015/0066042 | A1 * | 3/2015 | Cummins | A61B 17/7037 606/104 |
| 2016/0074075 | A1 | 3/2016 | Beyar et al. | |
| 2017/0129078 | A1 * | 5/2017 | Gatling | B25B 13/5091 |

FOREIGN PATENT DOCUMENTS

| | | |
|---|---|---|
| DE | 4238339 C2 | 5/1994 |
| DE | 10005386 A1 | 8/2001 |
| FR | 2650173 A1 | 2/1991 |
| FR | 2659546 A1 | 9/1991 |
| FR | 0571619 B1 | 12/1993 |
| FR | 2778089 A1 | 11/1999 |
| WO | 9410944 A1 | 5/1994 |
| WO | 9514437 A1 | 6/1995 |
| WO | 2011133160 A1 | 10/2011 |
| WO | 2012057386 A1 | 5/2012 |
| WO | 2014142797 A1 | 9/2014 |
| WO | 2014204076 A1 | 12/2014 |

\* cited by examiner

PEDICLE SCREW REMOVAL TOOL AND METHOD OF USE

FIELD OF THE DISCLOSURE

The present disclosure relates to tools for use during spinal surgery. In particular, the present disclosure relates to a pedicle screw removal tool.

BACKGROUND OF THE DISCLOSURE

Spinal fusion, also called spondylodesis or spondylosyndesis, is a neurosurgical surgical technique that joins two or more vertebrae. Supplementary bone tissue or artificial bone is used to augment natural bone growth processes to fuse two or more adjoining vertebrae. When additional stability is required, vertebrae can be stabilized with screws through the pedicles of each vertebra and connected with a stability rod.

Figure 1:
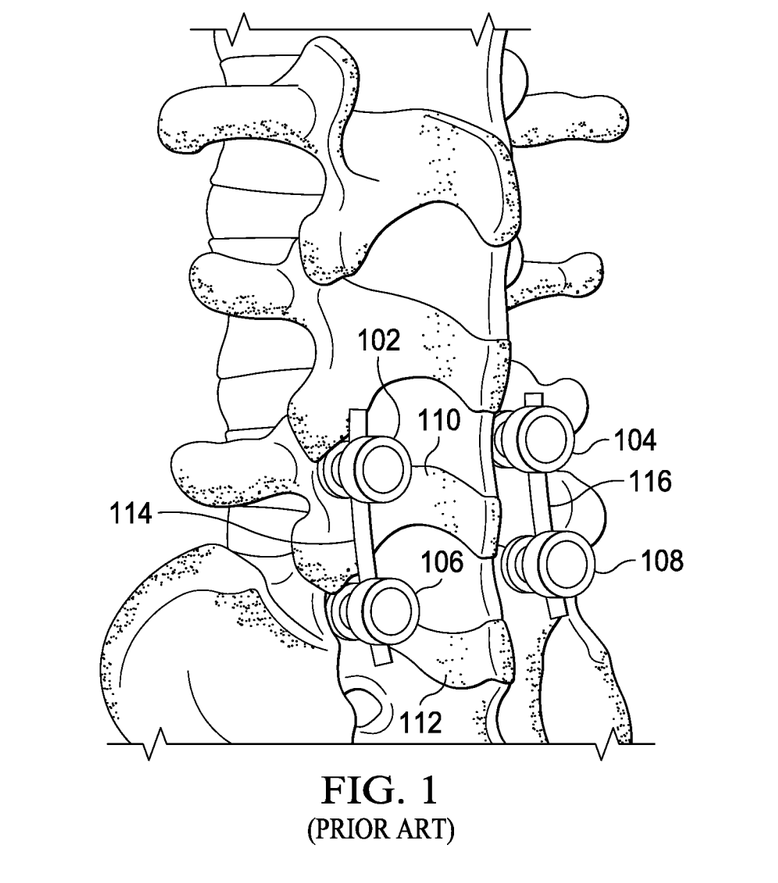
FIG. 1 is an isometric view of vertebrae anchored by pedicle screws and stability rods as known in the prior art.

FIG. 1 shows four pedicle screws 102, 104, 106, and 108 anchored in the pedicles of two adjoining vertebrae 110 and 112. Stability rod 114 is anchored by pedicle screws 102 and 106. Stability rod 116 is anchored by pedicle screws 104 and 108.

A pedicle screw is a particular type of bone screw designed for implantation during a spinal fusion procedure. A common type of pedicle screw is a "tuliped" pedicle screw that is comprised of a "U" shaped body affixed to a threaded section. The "U" shaped body presents a channel for seating the rod. A threaded end cap engages the body to secure the rod to the screw. The body includes a machined recess shaped for receiving a screwdriver type tool which is used to implant and remove the pedicle screw.

Figure 2A:
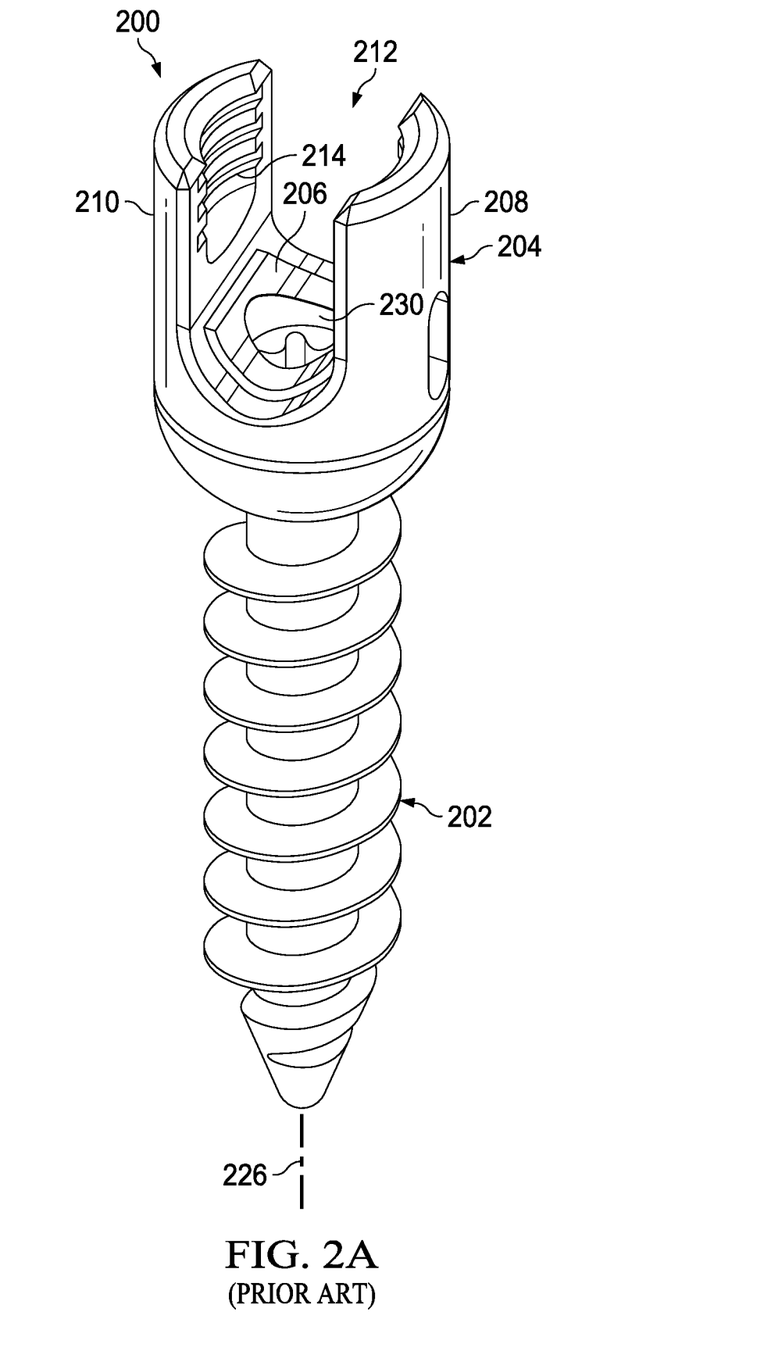
FIG. 2A is an isometric view of a tuliped pedicle screw as known in the prior art.
Figure 2B:
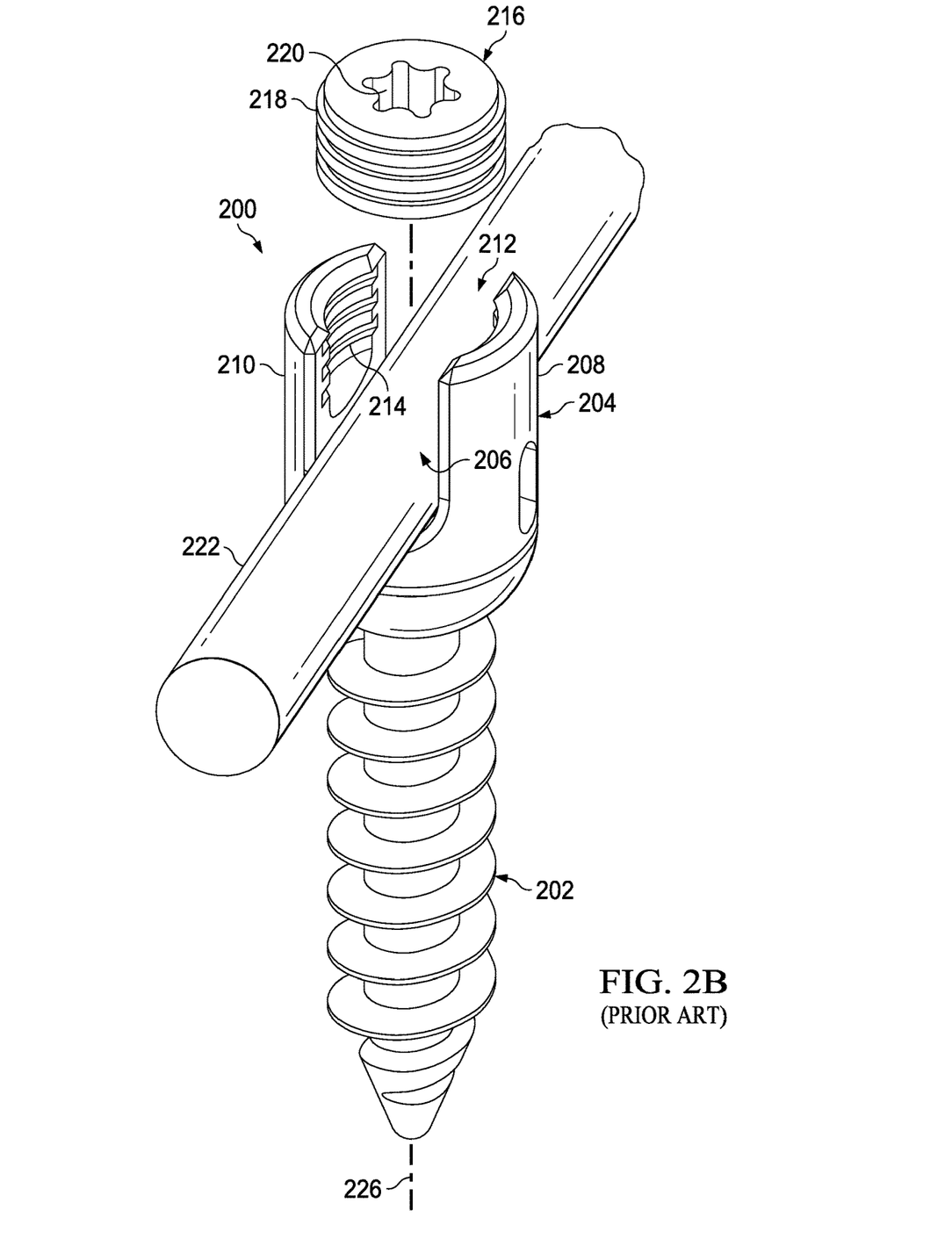
FIG. 2B is an exploded isometric view of a tuliped pedicle screw engaged with a stability rod as known in the prior art.

Referring to FIGS. 2A and 2B, the components of a common tuliped pedicle screw are shown. Pedicle screw 200 comprises threaded section 202 connected to body 204. Threaded section 202 has longitudinal axis 226. Body 204 forms channel 206 between blades 208 and 210. Body 204 includes opening 212 opposite threaded section 202. Opening 212 leads to channel 206. At the base of the channel, the tuliped pedicle screw includes socket 230 used to install the screw into bone. Internal thread 214 is formed on each blade 208 and 210 proximate opening 212. End cap 216 is disc shaped and includes exterior thread 218 sized to engage internal thread 214. End cap 216 further defines socket 220 shaped to receive a screwdriver type tool. Rod 222 fits within channel 206. End cap 216 is threadably engaged with body 204 and secures rod 222 to pedicle screw 200.

Occasionally it is necessary to remove the pedicle screws after successful spinal fusion and stability are achieved. During surgery, a universal removal tray is utilized. The tray is equipped with many tools necessary to accommodate the different sizes and shapes of pedicle screws. Removal can be difficult because often the screws have become incarcerated in the bone and will not turn easily. Further, the body socket is many times filled with boney growth. The boney growth makes insertion of a removal tool difficult. As a result, the channel and the body socket is often stripped, bent, or broken during the removal procedure.

Several techniques have been developed to effect removal of a pedicle screw once its integrity is compromised. For example, one technique involves bisecting the stability rod, and securing it to the screw with an end cap. Pliers are then used to hold the rod and apply torque to the screw. This method creates a problem because ends of the rod can cause damage to the surrounding tissue leading to substantial bleeding and prolonged recovery time. As a second example, a cutting wheel may be used to notch the top of the screw in order to facilitate the use of a bladed removal tool. A problem with this approach is that metal shavings resulting from the procedure resist removal through irrigation and can contaminate the surrounding tissue. A more serious problem is that the cutting wheel, if not used carefully, may damage the spinal cord causing paralysis.

Hence, there is a need for a pedicle screw removal device that can be universally used for all sizes and shapes of tuliped pedicle screws that will function to cleanly remove a compromised screw without risk of contamination or damage to surrounding tissues.

SUMMARY OF THE DISCLOSURE

A preferred embodiment is comprised of a tapered shaft having a right angle removal tip formed as its distal end and a generally square head on the proximal end. The removal tip is integrally formed with a tapered section which expands the overall circumference of the shaft. The tapered section leads to a cylindrically shaped handle section. The handle section may include a set of serrations. The removal tip is sized to match a stability rod and to easily engage the channel of a tuliped pedicle screw. The square head is designed to accommodate a ratchet or "T" handle.

In an alternate embodiment, the removal tip includes opposing prongs.

In another alternate embodiment, the handle section includes opposing members extending from the shaft to form a "T" shaped handle. Any combination of the alternate embodiments of the tip and handle is envisioned.

In use, the removal tip is inserted into the channel of a tuliped pedicle screw and secured to the screw with an end cap. The shaft is rotated via the handle section or with a torque producing tool attached to the head. The shaft is rotated along its longitudinal axis in a rotational direction that unscrews the pedicle screw from the bone. The removal tip eliminates the need for removal of boney tissue from the body socket or, alternatively, is useful after the body socket is compromised during removal.

Those skilled in the art will appreciate the above-mentioned features and advantages of the disclosure together with other important aspects upon reading the detailed description that follows in conjunction with the drawings.

DETAILED DESCRIPTION

In the description that follows, like parts are marked throughout the specification and figures with the same numerals, respectively. The figures are not necessarily drawn to scale and may be shown in exaggerated or generalized form in the interest of clarity and conciseness.

Figure 3A:
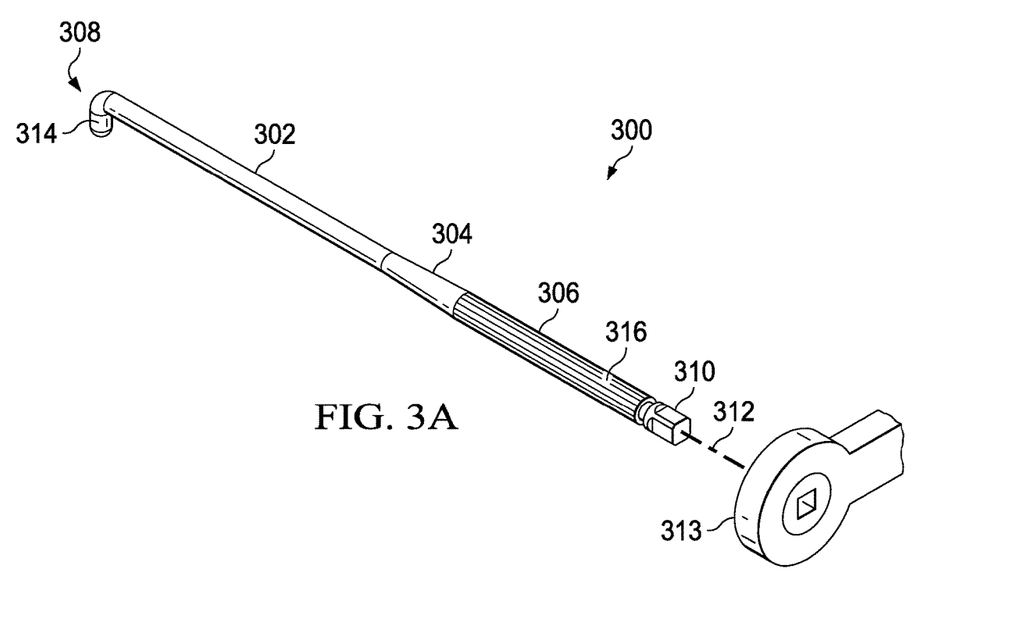
FIG. 3A is an isometric view of a preferred embodiment.
Figure 3B:
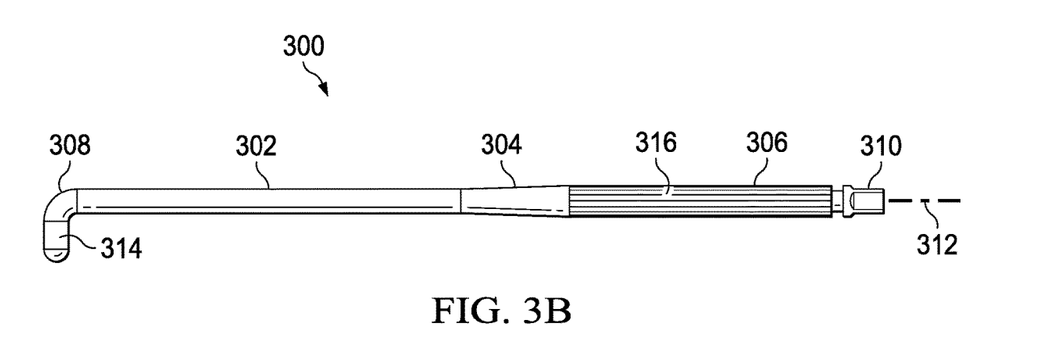
FIG. 3B is a side view of the preferred embodiment of FIG. 3A.

Referring to FIGS. 3A and 3B, pedicle screw removal tool 300 is a generally tapered cylindrical shaft comprising lower section 302 integrally formed with neck 304. Neck 304 is integrally formed with handle 306. Tip 308 is integrally formed with lower section 302 opposite neck 304. Head 310 is integrally formed with handle 306 opposite neck 304. Torque imposing tool 313 is removably attached to the head. The torque imposing tool may be, for example, a ratchet adaptor which applies torque in only one rotational direction. In another example, the torque imposing tool can be a simple crescent wrench. In yet another example, the torque imposing tool can be a torque wrench indicating the amount of torque applied to prevent shearing of the pedicle screw shaft. Lower section 302 is axially aligned with neck 304. Neck 304 is axially aligned with handle 306. Handle 306 is axially aligned with head 310. Lower section 302, neck 304, handle 306, and head 310 all share central longitudinal axis 312. Tip 308 is generally "L" shaped formed by prong 314. Prong 314 extends from tip 308 generally perpendicular to lower section 302. In a preferred embodiment, pedicle screw removal tool 300 is constructed of surgical grade stainless steel.

The overall length of pedicle screw removal tool 300 can range from approximately eight to twelve inches depending on desired use. Prong 314 generally ranges from ⅛ to ½ inch in diameter. The length of prong 314 ranges from approximately ½ to one inch. Lower section 302 ranges in length from approximately three to five inches. Lower section 302 generally ranges from ⅛ to ½ inch in diameter. The length of neck 304 ranges from approximately one to two inches. Neck 304 is a generally frustoconical shape with an increasing diameter from a range of ⅛ to ½ inch in diameter at the connection of neck 304 to lower section 302 to a range of ½ inch to ¾ inch in diameter at the connection of neck 304 to handle 306. Handle 306 ranges in length from approximately three to four inches. Handle 306 generally ranges from ½ to ¾ inch in diameter. In an alternate embodiment, handle 306 may include serrations 316. Head 310 ranges in length from approximately ½ to one inch. Head 310 has a generally square cross-section width a width that ranges from approximately ½ to ¾ of an inch. In alternate embodiments, head 310 may have other polygonal cross-sectional shapes suitable for attachment of the torque imposing tool.

Figure 4:
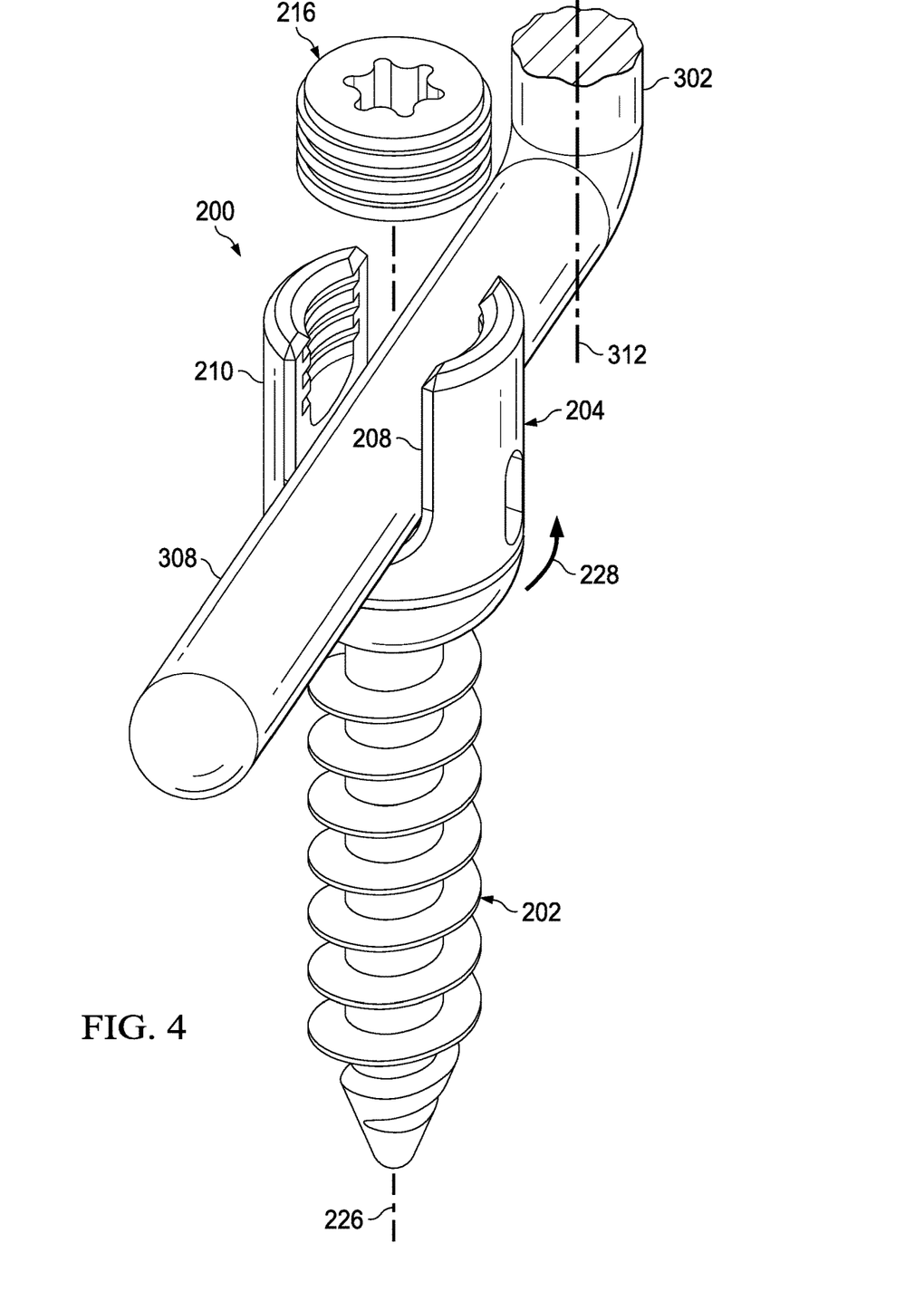
FIG. 4 is an isometric view of the preferred embodiment of FIG. 3A engaged with a tuliped pedicle screw.

As shown in FIG. 4, pedicle screw removal tool 300 can be used to remove tuliped pedicle screw.

After clearing away any residual tissue from the pedicle screw, end cap 216 is removed. Next, stability rod 222 is removed. Removal of additional tissue surrounding body 204 of pedicle screw 200 is then accomplished. Tip 308 is inserted into channel 206 such that prong 314 is adjacent blades 208 and 210. Longitudinal axis 312 of pedicle screw removal tool 300 is positioned generally coplanar and parallel with longitudinal axis 226 of threaded section 202. Longitudinal axis 312 of pedicle removal tool 300 is generally positioned offset from longitudinal axis 226 of threaded section 202 such that the axes are not axially aligned. End cap 216 is reengaged with body 204 to secure tip 308 to pedicle screw 200. Optionally, end cap 216 remains disengaged from body 204. In the event that end cap 216 is compromised and cannot be removed, tip 308 is inserted into channel 206 from the side and underneath end cap 216. Pedicle screw removal tool 300 is rotated in direction 228 around pedicle screw 200, generally counter-clockwise, to unscrew pedicle screw 200 from the bone. Rotation of pedicle screw removal tool 300 can be accomplished by use of handle 306 or, if necessary, a torque producing tool such as a ratchet attached to head 310.

Use of pedicle screw removal tool 300 eliminates the need to locate a matching removal tool for the pedicle screw regardless of whether or not the socket has been compromised. This procedure improves the speed and accuracy of pedicle screw removal as time is not wasted locating the proper sized tool, or fabricating custom tools. Further, safety is improved by reducing time required attending to unnecessary tissue damage and contamination.

Figure 5:
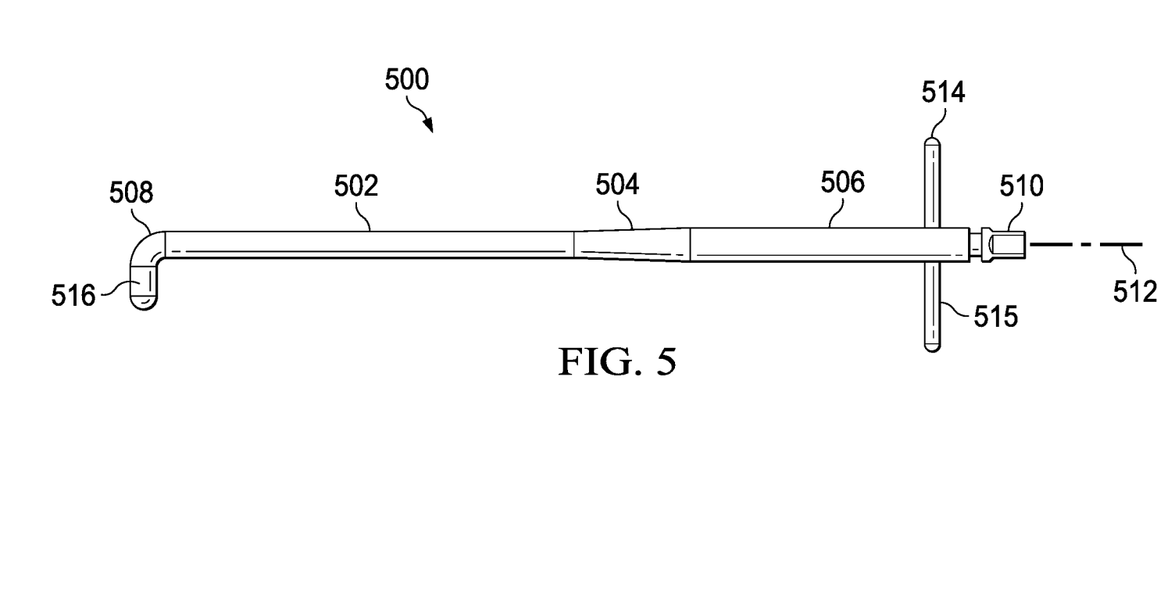
FIG. 5 is a side view of an alternate preferred embodiment.

Referring to FIG. 5, an alternate embodiment will be described. Pedicle screw removal tool 500 is a generally cylindrical shaft comprising lower section 502 integrally formed with and connected to neck 504. Neck 504 is integrally formed with and connected to handle 106. Neck 504 radially expands from lower section 502 to handle 506. Tip 508 is integrally formed with and connected to lower section 502 opposite neck 504. Head 510 is integrally formed with and connected to handle 506 opposite neck 504. Lower section 502 is axially aligned with neck 504. Neck 504 is axially aligned with handle 506. Handle 506 is axially aligned with head 510. Lower section 502, neck 504, handle 506, and head 510 all share central longitudinal axis 512. Handle 506 further includes opposing members 514 and 515. Tip 508 is generally "L" shaped formed by prong 516. Prong 516 extends from tip 508 generally perpendicular to lower section 502. In a preferred embodiment, pedicle screw removal tool 500 is constructed of surgical grade steel.

The overall length of pedicle screw removal tool 500 can range from approximately eight to twelve inches depending on desired use. Prong 516 generally ranges from ⅛ to ½ inch in diameter. The length of prong 516 ranges from approximately ½ to one inch. Lower section 502 ranges in length from approximately three to five inches. Lower section 502 generally ranges from ⅛ to ½ inch in diameter. The length of neck 504 ranges from approximately one to two inches. Neck 504 is a generally frustoconical shape with an increasing diameter from a range of ⅛ to ½ inch in diameter at the connection of neck 504 to lower section 502 to a range of ½ inch to ¾ inch in diameter at the connection of neck 504 to handle 506. Handle 506 ranges in length from approximately three to four inches. Handle 506 generally ranges from ½ to ¾ inch in diameter. Members 514 and 515 are generally cylindrical (however, other cross-sections are envisioned), are axially aligned, and extend from handle 506 generally perpendicular to handle 506. Members 514 and 515 each range in length from approximately one and ½ to two inches. Members 514 and 515 generally range from ½ to ¾ inch in diameter. Head 510 ranges in length from approximately ½ to one inch. Head 510 has a generally square cross-section width a width that ranges from approximately ½ to ¾ of an inch. In alternate embodiments, head 510 may have other polygonal cross-sectional shapes suitable for attachment of a torque producing tool.

In use, in addition to the previous methods discussed, members 514 and 515 may be used to assist in the rotation of pedicle screw removal tool 500 in order to remove tuliped pedicle screws.

Figure 6:
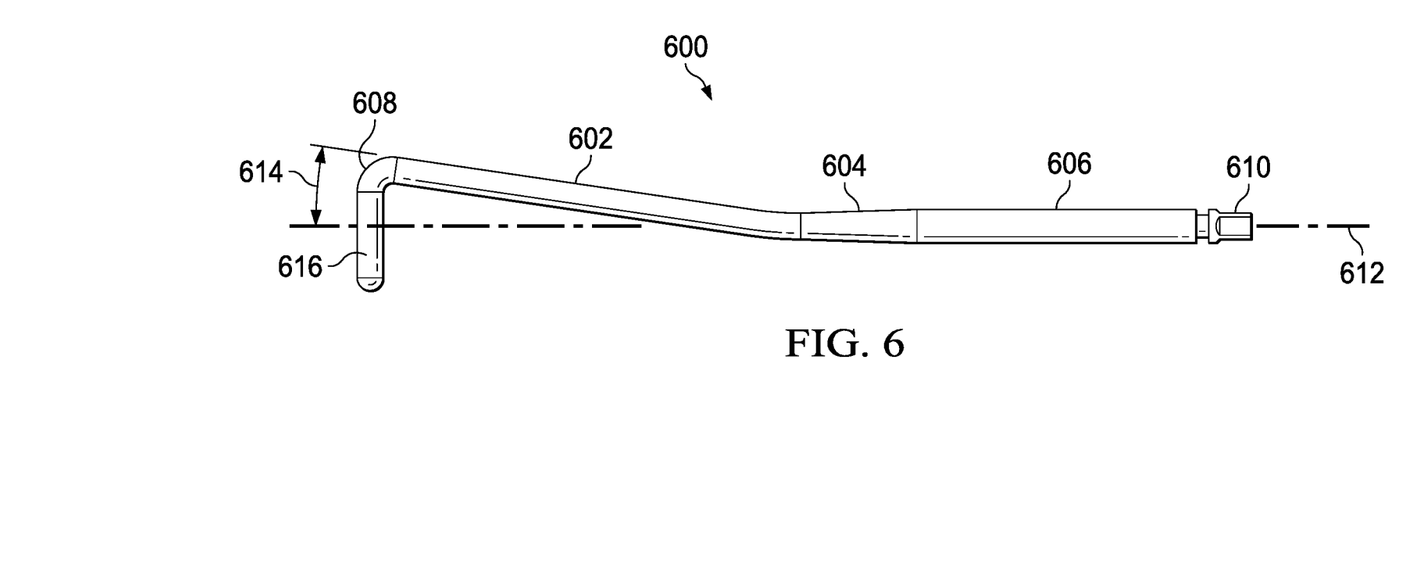
FIG. 6 is a side view of an alternate preferred embodiment.

Referring to FIG. 6, an alternate embodiment will be described. Pedicle screw removal tool 600 is a generally tapered cylindrical shaft comprising an angled lower section 602 integrally formed with neck 604. Neck 604 is integrally formed with handle 606. Tip 608 is integrally formed with lower section 602 opposite neck 604. Head 610 is integrally formed with handle 606 opposite neck 604. Lower section 302 extends at angle 614 from neck 604. Neck 604 is axially aligned with handle 606. Handle 606 is axially aligned with head 610. Neck 604, handle 606, and head 610 all share central longitudinal axis 612. Tip 608 is generally "L" shaped formed by prong 616. Prong 616 extends from tip 608 generally perpendicular to longitudinal axis 612. Longitudinal axis 612 intersects prong 616. In a preferred embodiment, pedicle screw removal tool 600 is constructed of surgical grade stainless steel.

The overall length of pedicle screw removal tool 600 can range from approximately eight to twelve inches depending on desired use. Prong 616 generally ranges from ⅛ to ½ inch in diameter. The length of prong 616 ranges from approximately ½ to one inch. Lower section 602 ranges in length from approximately three to five inches. Lower section 602 generally ranges from ⅛ to ½ inch in diameter. Angle 614 ranges from approximately 15° to 45°. The length of neck 604 ranges from approximately one to two inches. Neck 604 is a generally frustoconical shape with an increasing diameter from a range of ⅛ to ½ inch in diameter at the connection of neck 604 to lower section 602 to a range of ½ inch to ¾ inch in diameter at the connection of neck 604 to handle 606. Handle 606 ranges in length from approximately three to four inches. Handle 606 generally ranges from ½ to ¾ inch in diameter. Head 610 ranges in length from approximately ½ to one inch. Head 610 has a generally square cross-section width a width that ranges from approximately ½ to ¾ of an inch. In alternate embodiments, head 610 may have other polygonal cross-sectional shapes suitable for attachment of a torque producing tool.

Figure 7:
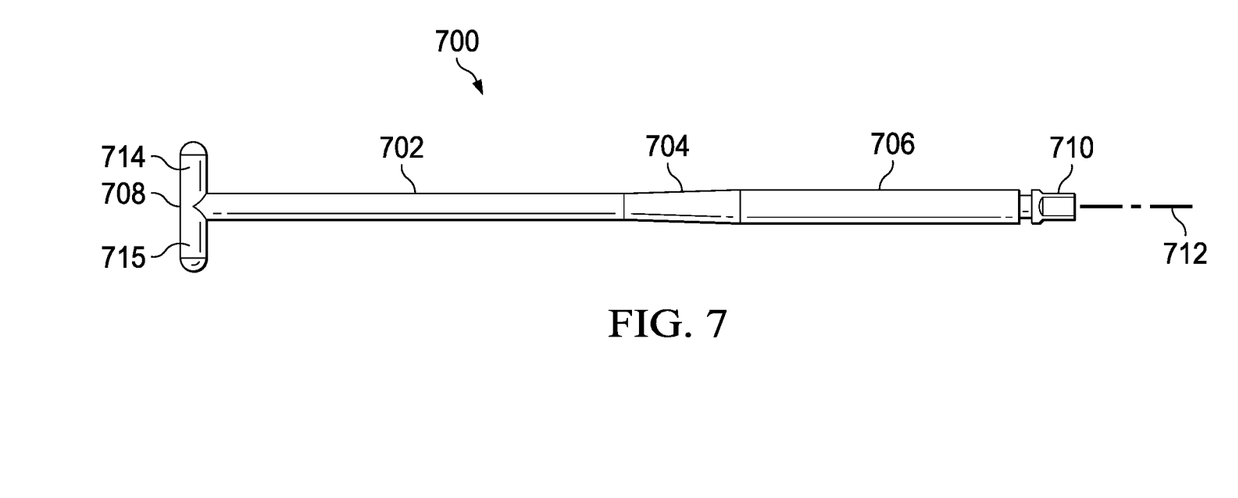
FIG. 7 is a side view of an alternate preferred embodiment.

Referring to FIG. 7, an alternate embodiment will be described. Pedicle screw removal tool 700 is a generally tapered cylindrical shaft comprising lower section 702 integrally formed with and connected to neck 704. Neck 704 is integrally formed with and connected to handle 706. Tip 708 is integrally formed with and connected to lower section 702 opposite neck 704. Head 710 is integrally formed with and connected to handle 706 opposite neck 704. Lower section 702 is axially aligned with neck 704. Neck 704 is axially aligned with handle 706. Handle 706 is axially aligned with head 710. Lower section 702, neck 704, handle 706, and head 710 all share longitudinal axis 712. Tip 708 is generally "T" shaped formed by prongs 714 and 715. Prongs 714 and 715 are axially aligned and extend from tip 708 generally perpendicular to lower section 702. In a preferred embodiment, pedicle screw removal tool 700 is constructed of surgical grade stainless steel.

The overall length of pedicle screw removal tool 700 can range from approximately eight to twelve inches depending on intended use. Prong 714 and 715 generally range from ⅛ to ½ inch in diameter. The length of each prong 714 and 715 ranges from approximately ¼ to ½ inch. Lower section 702 ranges in length from approximately three to five inches. Lower section 702 generally ranges from ⅛ to ½ inch in diameter. The length of neck 704 ranges from approximately one to two inches. Neck 704 generally expands from a range of ⅛ to ½ inch in diameter at the connection of neck 704 to lower section 702 to a range of ½ inch to ¾ inch in diameter at the connection of neck 704 to handle 706. Handle 706 ranges in length from approximately three to four inches. Handle 706 generally ranges from ½ to ¾ inch in diameter. Head 710 ranges in length from approximately ½ to one inch. Head 710 has a generally square cross-section width a width that ranges from approximately ½ to ¾ of an inch. In alternate embodiments, head 710 may have other polygonal cross-sectional shapes suitable for attachment of a torque producing tool.

Figure 8:
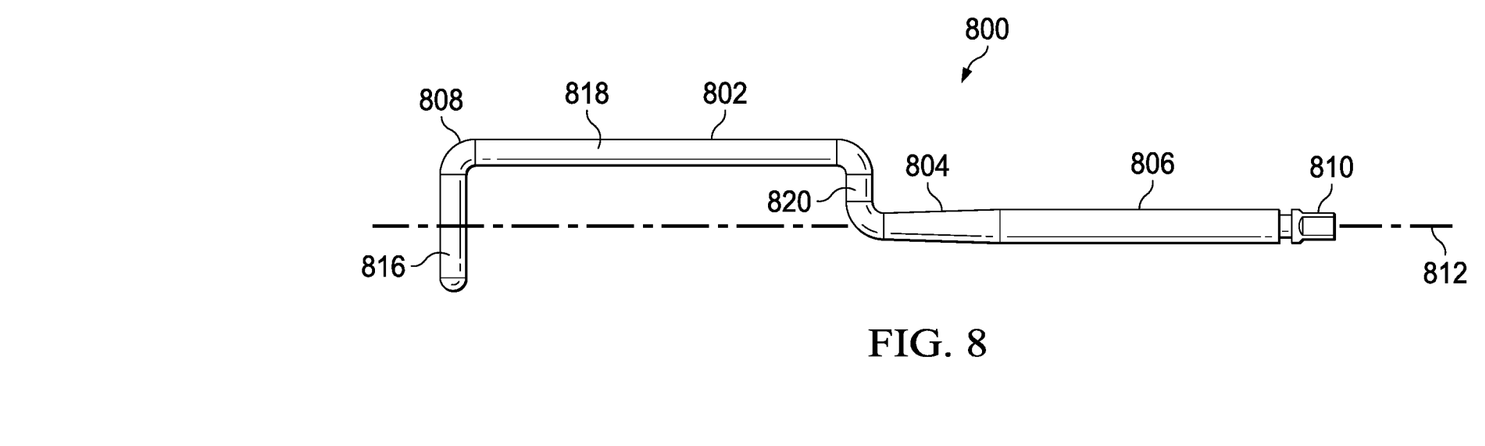
FIG. 8 is a side view of an alternate preferred embodiment.

Referring to FIG. 8, an alternate embodiment will be described. Pedicle screw removal tool 800 is a generally tapered cylindrical shaft comprising a offset lower section 802 integrally formed with neck 804. Neck 804 is integrally formed with handle 806. Tip 808 is integrally formed with lower section 802 opposite neck 804. Head 810 is integrally formed with handle 806 opposite neck 804. Neck 804 is axially aligned with handle 806. Handle 806 is axially aligned with head 810. Neck 804, handle 806, and head 810 all share central longitudinal axis 812. Lower section 802 comprises segments 818 and 820. Segment 818 is generally parallel with longitudinal axis 812 and connects segment 820 to tip 808. Segment 820 extends generally perpendicular to longitudinal axis 812 from neck 804. Prong 816 extends from segment 818 generally perpendicular to longitudinal axis 812. Longitudinal axis 812 intersects prong 816. In a preferred embodiment, pedicle screw removal tool 800 is constructed of surgical grade stainless steel.

The overall length of pedicle screw removal tool 800 can range from approximately eight to twelve inches depending on desired use. The length of prong 816 ranges from approximately ½ to one inch. Prong 816 generally ranges from ⅛ to ½ inch in diameter. Lower section 802 ranges in length from approximately three to five inches. Lower section 802 generally ranges from ⅛ to ½ inch in diameter. Segment 820 ranges in length from approximately ½ to one inch. Segment 820 generally ranges from ⅛ to ½ inch in diameter. The length of neck 804 ranges from approximately one to two inches. Neck 804 is a generally frustoconical shape with an increasing diameter from a range of ⅛ to ½ inch in diameter at the connection of neck 804 to lower section 802 to a range of ½ inch to ¾ inch in diameter at the connection of neck 804 to handle 806. Handle 806 ranges in length from approximately three to four inches. Handle 806 generally ranges from ½ to ¾ inch in diameter. Head 810 ranges in length from approximately ½ to one inch. Head 810 has a generally square cross-section width a width that ranges from approximately ½ to ¾ of an inch. In alternate embodiments, head 810 may have other polygonal cross-sectional shapes suitable for attachment of a torque producing tool.

Pedicle screw removal tools 600, 700, and 800 can each be used to remove any size tuliped pedicle screw.

In use end cap 216 is removed. Rod 222 is removed. Tissue surrounding body 204 of the pedicle screw is removed. When using tool 600, tip 608 is inserted into channel 206 such that prong 616 is adjacent blades 208 and 210. When using tool 700, tip 708 is inserted into channel 206 such that prongs 714 and 715 are adjacent blades 208 and 210. When using tool 800, tip 808 is inserted into channel 206 such that prong 816 is adjacent blades 208 and 210. Depending on which tool is in use, longitudinal axis 612, 712, or 812 is positioned generally coaxial with longitudinal axis 226 of threaded section 202. The pedicle screw removal tool is rotated, generally counter-clockwise, to dislodge pedicle screw 200 from its attachment to the bone. Rotation of the pedicle screw removal tool can be accomplished by hand using the handle or, if necessary, a torque producing tool such as a wrench or ratchet can be attached to the head.

It will be appreciated by those skilled in the art that changes could be made to the embodiments described above without departing from the broad inventive concept thereof.

It is understood, therefore, that this disclosure is not limited to the particular embodiments disclosed, but it is intended to cover modifications within the spirit and scope of the present disclosure as defined by the appended claims.

The invention claimed is:

1. An apparatus comprising:
   a tuliped pedicle screw having a first longitudinal axis, a channel having a first blade and a second blade, an internal thread, and a threaded cap engaging the internal thread;
   a tuliped pedicle screw removal tool having:
      a shaft having a second longitudinal axis;
      the second longitudinal axis traversing the center of the shaft;
      a tip, connected to the shaft, having a prong extending perpendicularly from and coplanar with the second longitudinal axis of the shaft;
      the prong removably connected to the tuliped pedicle screw, in the channel, by the threaded cap;
      a handle connected to the shaft;
      a non-articulating, solid, polygonal head integral with and coaxial to the handle; and
   a torque imposing tool removably attached to the non-articulating, solid, polygonal head;
   wherein the second longitudinal axis is generally coplanar with the first longitudinal axis when the prong is connected to the channel of the tuliped pedicle screw; and,
   wherein rotation of the torque imposing tool rotates the tuliped pedicle screw.

2. The system of claim 1, wherein the second longitudinal axis is not collinear with the first longitudinal axis.

3. The system of claim 1, wherein the prong engages the first blade and the second blade.

4. The system of claim 1, wherein the torque imposing tool comprises a ratchet.

5. The system of claim 1, wherein the handle comprises a set of serrations.

6. The system of claim 1,
   wherein the shaft is cylindrical and has a first diameter;
   wherein the handle is cylindrical and has a second diameter; and,
   wherein the second diameter is greater than the first diameter.

7. The system of claim 1, wherein the non-articulating, solid, polygonal head has a square cross-section.

8. The system of claim 1, further comprising:
   a neck connected to the shaft at a first connection point;
   the neck connected to the handle at a second connection point; and,
   wherein the neck is generally frustoconically shaped having an increasing diameter between the first connection point and the second connection point.

9. A system comprising:
   a tuliped pedicle screw having a first longitudinal axis and a channel; and
   a tuliped pedicle screw removal tool having:
      a shaft with a first end and a second end;
      a handle, having a second longitudinal axis, central to the shaft, connected to the first end;
      a non-articulating, solid, polygonal head, coaxial with the second longitudinal axis, integrally formed with the handle, and removably attached to a torque imposing tool;
      a prong, integrally formed on the second end, and removably connected to the channel;
      the prong extending from the tip perpendicularly from and coplanar with the second longitudinal axis;
   wherein the first longitudinal axis is generally coplanar with the second longitudinal axis when the prong is connected to the channel of the tuliped pedicle screw; and,
   wherein rotation of the torque imposing tool rotates the tuliped pedicle screw.

10. The system of claim 9, further comprising:
    a set of serrations formed in the handle.

11. The system of claim 9, wherein the second longitudinal axis is not collinear with the first longitudinal axis.

12. A system comprising:
    a tuliped pedicle screw having a first longitudinal axis, a channel having a first blade and a second blade, an internal thread, and a threaded cap engaging the internal thread;
    a pedicle screw removal tool having:
       a shaft having a second longitudinal axis, central to the shaft, a first end and a second end;
       wherein the shaft is cylindrical and has a first diameter;
       a tip integrally formed on the second end of the shaft, having a prong extending perpendicularly with respect to the second longitudinal axis of the shaft;
       the prong engaging the first blade and the second blade and being removably fixed to the tuliped pedicle screw, in the channel, by the threaded cap;
       a neck, having a first connection point and a second connection point, connected to the first end of the shaft at the first connection point;
       wherein the neck is frustoconically shaped having an increasing diameter between the first connection point and the second connection point;
       a handle connected to the neck at the second connection point;
       wherein the handle comprises a set of serrations;
       wherein the handle is cylindrical and has a second diameter;
       wherein the second diameter is greater than the first diameter;
       a non-articulating, solid, polygonal head integral with and coaxial to the handle; and
    a torque imposing tool removably attached to the non-articulating, solid, polygonal head;
    wherein the torque imposing tool comprises a ratchet;
    wherein the second longitudinal axis is coplanar and not collinear with the first longitudinal axis when the prong is fixed to the channel of the tuliped pedicle screw; and wherein rotation of the torque imposing tool rotates and removes the tuliped pedicle screw.

* * * * *